(12) United States Patent
Barkan et al.

(10) Patent No.: US 7,109,159 B1
(45) Date of Patent: Sep. 19, 2006

(54) LEPTIN AS AN INHIBITOR OF TUMOR CELL PROLIFERATION

(75) Inventors: Dalit Barkan, Rehovot (IL); Batya Cohen, Tel Aviv (IL); Menachem Rubinstein, Givat Shmuel (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/403,897

(22) PCT Filed: Apr. 26, 1998

(86) PCT No.: PCT/IL98/00196

§ 371 (c)(1),
(2), (4) Date: Feb. 22, 2000

(87) PCT Pub. No.: WO98/48831

PCT Pub. Date: Nov. 5, 1998

(30) Foreign Application Priority Data

Apr. 29, 1997 (IL) .................................... 120733

(51) Int. Cl.
*A61K 38/00* (2006.01)
(52) U.S. Cl. ............................................ 514/2; 514/21
(58) Field of Classification Search ................ 514/2, 514/21; 530/350
See application file for complete search history.

(56) References Cited

U.S. PATENT DOCUMENTS 5,756,461 A * 5/1998 Stephens ..................... 514/12

OTHER PUBLICATIONS

Rubinstein et al, "Leptin inhibits growth factor induced cell proliferation." Cytokine, vol. 9, No. 11, p. 953, Abstract 253, Nov. 1997.*
Jackson, JG and White MF, "Insulin receptor substrate-1 is the predominant signaling molecule activated by insulin-like growth factor-1 . . . " J. of Biological Chemistry, vol. 273, No. 16, pp. 9994-10003, Apr. 1998.*
Bjorbaek et al, "Divergent Signaling Capacities of the Long and short Isoforms of the Leptin Receptor.", J or Biological Chemistry, vol. 272, No. 51, pp. 32686-32695, Dec. 1997.*
Bowie et al "Deciphering the Message in protein Sequences:Tolerance to Amino Acid substitutions" Science, vol. 247, pp. 1306-1310, 1990.*
Lazar et al, "Transforming Growth Factor Alpha: Mutation of Aspartic Acid 47 and Leuine 48 Results in Different Biological Activities", Molecular and Cellular Biology, vol. 8, pp. 1247-1252, 1988.*
Burgess et al "Possible Dissociation of the Heparin-binding and Mitogenic Activities of Heparin-binding Growth Factor-1 from Its Receptor-binding Activities by Site-directed Mutagenesis of a single Lysine Residue", Journal of Cellular biology, vol. 111, pp., 1990.*
P. Bork, "Power and pitfalls in sequenc analysis", Genome Research, vol. 10, pp. 398-400, 2000.*
Gura, T. "systems for identifying new drugs are often faulty", Science, vol. 278, pp. 1041-1042, Nov. 1997.*
Jain, R., "Barriers to drug delivery in solid tumors", Scientific American, vol. 271, pp. 58-65, Jul. 1994.*
Curti, B., "Physical Barriers to drug delivery in tumors", Critical Reviews in Oncology/Hematology, vol. 14, pp. 29-39, 1993.*
Hartwell et al, "Integrating genetic approaches into the discovery of anticancer drugs", Scienc, vol. 278, pp. 1064-1068, Nov. 1997.*
Mathews and Van Holde, Biochemistry (textbook), 2nd edition, pp. 165-171, 1996.*
B. Matthews, "Genetic and Structural analysis of the protein stability problem", in Perspectives in Biochemistry, vol. 1, pp. 6-9, 1989.*
Rubinstein et al, Cytokine, 1997, vol. 9, pp. 953, abstract only.*
Moro et al, Journal of biological chemistry, 1999, vol. 274, pp. 23103-23110. (abstract).*
Tanaka et al (Journal of Biological Chemistry, Jun. 14, 1996, vol. 24, pp. 14610-14616).*
The abstract of Stevenson et al (Proc Annu Meet Am Assoc Cancer Res, 1996, vol. 37, p. A375).*
Clark et al (International Journal of Cancer, 1996, vol. 65, pp. 186-191).*
Carter et al (U.S. Patent Application 2002193571, priority to Jan. 7, 1997).*
Abstract of Sastry et al (International Journal of Cancer, Jan. 17, 1997, vol. 70, No. 2, pp. 208-213).*
Abstract of Janes et al (Oncogene, Dec. 1994, vol. 9, No. 12, pp. 3601-3608).*
Abstract of Fiddes et al (Cell Growth and Differentiation, 1995, vol. 6, No. 12, pp. 1567-1577).*
Abstract of Ito et al (Molecular and Cellular Biology, 1996, vol. 16, No. 3, pp. 943-951).*
Zachow et al., Direct Intraovarian Effects of Leptin: Impairment of the Synergistic Action of Insulin-like Growth Factor-I on Follicle-Stimulating Hormone-Dependent Estradiol-17 Production by Rat Ovarian Granulosa Cells, *"Endocrinology"*, vol. 138, No. 2, pp. 847-850, (1997).
Barkan et al., "Leptin Inhibits Growth-Factor-Induced Cell Proliferation", *Chemical Abstracts*, pp. 953, (1997).

* cited by examiner

*Primary Examiner*—Karen A. Canella
(74) *Attorney, Agent, or Firm*—Browdy and Neimark, PLLC

(57) ABSTRACT

The use of leptin and leptin-related molecules in oncology is disclosed.

18 Claims, 9 Drawing Sheets

US 7,109,159 B1

LEPTIN AS AN INHIBITOR OF TUMOR CELL PROLIFERATION

CROSS REFERENCE TO RELATED APPLICATION

The present application is the national stage under 35 U.S.C. 371 of PCT/IL98/00196, filed Apr. 26, 1998.

FIELD OF THE INVENTION

The present invention relates to leptin, a cytokine produced by adipocytes and affecting a variety of cells and tissues. More particularly, this invention relates to novel applications of leptin in the field of oncology.

BACKGROUND OF THE INVENTION

Leptin, an adipocyte-derived cytokine that regulates body weight, was identified by positional cloning of the murine ob gene (Zhang et al., 1994) and was shown to affect both food intake and thermogenesis (Campfield et al., 1995; Collins et al., 1996; Halaas et al, 1995; Pelleymounter et al., 1995; Weigle et al., 1995). High affinity leptin-binding sites were located in the choroid plexus; expression cloning of cDNA from this tissue provided the leptin receptor (OB-R) (Tartaglia et al., 1995). The known activities of leptin are mediated through its receptor in the hypothalamus. Leptin receptors are expressed, nonetheless, in additional organs, notably the kidney, lung and liver (Cioffi et al., 1996; Lee et al., 1996; Tartaglia et al., 1995). Furthermore, a different repertoire of leptin receptor-splice variants, differing in their cytoplasmic domain, is expressed in a tissue-specific manner in the mouse (Lee et al., 1996). Therefore, in addition to control of food intake and body heat, leptin may exert other physiological functions.

Although leptin is produced by adipocytes, the recent finding of a correlation between excess fat and high levels of leptin in the serum was in contrast with the notion that leptin reduces food intake and body weight (Considine et al., 1996; Frederich et al., 1995; Lonnqvist et al., 1995; Maffei et al., 1995). This correlation, and the well established linkage between obesity and insulin resistance (Felber and Golay, 1995), suggested that leptin may modulate insulin-regulated responses. Indeed, it was recently reported that leptin reduced significantly the basal and insulin-induced tyrosine-phosphorylation of the insulin receptor substrate-1 (IRS-1). This effect of leptin on IRS-1 phosphorylation was specific, since tyrosine-phosphorylation of the insulin receptor (IR) β-chain was not reduced (Cohen et al., 1996).

Tyrosine-phosphorylation of IRS-1 by the IR kinase is a key step in the insulin receptor signaling cascade, leading to many of the known insulin activities (Araki et al., 1994; Cheatham and Kahn, 1995; Myers et al., 1994; Myers et al., 1994; Myers and White, 1993; Rose et al., 1994; Tamemoto et al., 1994; White and Kahn, 1994). Downstream signaling of IRS-1 is mediated by several associated proteins, one of which is the Growth-factor Receptor-associated Binding protein-2 (GRB2) (Cheatham and Kahn, 1995).

The insulin receptor (IR) is regarded as a metabolic receptor, mediating the effects of insulin on glucose homeostasis. As such it is expressed on terminally differentiated tissues such as adipose tissue, liver and muscle. However, many studies have shown that IR is a potent mitogenic receptor in vitro and in vivo when expressed in tumor cells. For instance, functional IRs were identified in several breast cancer cell lines, as determined by tyrosine-phosphorylation of the IR in response to insulin treatment. Furthermore, the IR mediates a mitogenic response in these cells, as determined by [$^3$H]thymidine incorporation (Milazzo et al., 1997; Millazzo et al., 1992).

Heretofore there has not been described the use of leptin in the field of oncology, in general; and in particular, leptin has not been described as being useful for inhibiting the proliferation of cells, especially proliferating cancer cells.

SUMMARY OF THE INVENTION

It is an object of the present invention to provide for the use of leptin as an inhibitor of cell proliferation, for example, to use leptin as an inhibitor of the proliferation of cancer cells.

It is another aim of the invention to provide for the use of leptin alone or in combination with other therapeutic agents for the treatment of various malignancies.

It is a further object of the present invention to provide for the use of leptin, leptin fusion proteins, leptin muteins, leptin receptor agonists, active fragments or fractions of any one thereof, active analogs or derivatives of any one thereof, salts of any one thereof, and mixtures of any thereof, for the treatment of various malignancies.

It is yet another object of the present invention to provide pharmaceutical compositions containing one or more of the above leptin, leptin fusion proteins, leptin muteins, leptin receptor agonists, active fragments or fractions of any one thereof, active analogs or derivatives of any one thereof, and salts of any one thereof, for the treatment of various malignancies.

Other objects of the present invention will be set forth herein below or will be readily apparent from the following disclosure.

The present invention provides the use of leptin as an inhibitor of cell proliferation. Leptin may be useful, either alone or in combination with other therapeutic agents or approaches, for the treatment of various malignancies. A preferred embodiment of the invention is the use of leptin for the inhibition of human breast carcinoma cell proliferation. The proliferation of many types of tumor cells is increased in the presence of various growth factors such as insulin and IGF-I. The growth stimulatory effect of insulin and IGF-I on cells is mediated, at least in part, via the IRS-1/GRB2 pathway (Myers et al., 1993). This pathway is inhibited by leptin. Furthermore, IRS-1 is a substrate of receptor kinases of additional growth factors and cytokines, including IL-4 and IL-9 (Pernis et al., 1995; Yin et al., 1995; Yin et al., 1994). Therefore, leptin may inhibit the mitogenic responses of some or all of the aforementioned growth factors and cytokines, as well as other growth factors, thereby inhibiting the proliferation of a variety of tumor cells. Examples provided include inhibition of the IGF-I-induced proliferation and insulin-induced proliferation of the human breast cancer cell lines T-47D and MCF7. The present invention also provides the use of leptin, leptin fusion proteins, leptin muteins, leptin receptor agonists, or active fragments or fractions of any one thereof, and salts of any one thereof as well as pharmaceutical compositions containing leptin, leptin fusion proteins, leptin muteins, leptin receptor agonists, active fragments or fractions of any one thereof, or salts of any one thereof for the treatment of various malignancies.

More specifically, the present invention provides the use of an active agent selected from the group consisting of leptin, leptin fusion proteins, leptin muteins, leptin receptor agonists, active fragments or fractions of any one thereof, active analogs or derivatives of any one thereof, salts of any one thereof, and mixtures of any thereof, as an inhibitor of tumor cell proliferation.

Embodiments of the above aspect of the present invention include:

(i) the use of the above active agent as an inhibitor of cell proliferation for the treatment of malignancies in mammals.

(ii) the use of the above active agent as an inhibitor of growth-factor dependent tumors.

(iii) the use of the above active agent as an inhibitor of human breast carcinoma cell proliferation.

(iv) the use of the above active agent for the treatment of human breast carcinomas.

(v) the use of the above active agent as an inhibitor of the growth stimulatory effect of insulin and IGF-I on tumor cells, as mediated, at least partially, by the insulin receptor substrate-1 (IRS-1)/growth-factor receptor-associated binding protein-2 (GRB2) pathway.

(vi) the use of the above active agent as an inhibitor of the mitogenic responses in tumor cells to one or more receptor kinases, growth factors and cytokines of the group consisting of IL-4 and IL-9, for all of which IRS-1 is a substrate, for the treatment of tumors.

(vii) the use of the above active agent as an inhibitor of basal, IGF-I-induced and insulin-induced tumor cell proliferation for the treatment of human breast cancers.

(viii) the use of the above active agent wherein said active ingredient is leptin, and said leptin is used as said inhibitor or for said treatment.

Likewise, the present invention also provides for an active agent selected from the group consisting of leptin, leptin fusion proteins, leptin muteins, leptin receptor agonists, active fragments or fractions of any one thereof, active analogs or derivatives of any one thereof, salts of any one thereof, and mixtures of any thereof, for use in the preparation of a medicament for the inhibition of tumor cell proliferation.

Embodiments of this aspect of the invention include:

(i) an active agent as above for use in the preparation of a medicament for the treatment of malignancies in mammals.

(ii) an active agent as above for use in the preparation of a medicament for the inhibition of growth-factor-dependent tumors.

(iii) an active agent as above for use in the preparation of a medicament for the inhibition of human breast carcinoma cell proliferation.

(iv) an active agent as above for use in the preparation of a medicament for the treatment of human breast carcinomas.

(v) an active agent as above for use in the preparation of a medicament for the inhibition of the growth stimulatory effect of IGF-I and insulin on tumor cells, as mediated, at least partially, by the IRS-1/GRB2 pathway.

(vi) an active agent as above for use in the preparation of a medicament for the inhibition of the mitogenic responses in tumor cells to one or more receptor kinases, growth factors and cytokines of the group consisting of IGF-I, IL-4 and IL-9, for all of which IRS-1 is a substrate, for the treatment of tumors.

(vii) an active agent as above for use in the preparation of a medicament for the inhibition of basal, IGF-I-induced and insulin-induced tumor cell proliferation, for the treatment of human breast cancers.

(viii) an active agent as above wherein said active agent is leptin, and said leptin is used for the preparation of said medicament.

Similarly, in another aspect, the present invention provides a pharmaceutical composition comprising as active ingredient an active agent as noted above and a pharmaceutically acceptable carrier, diluent or excipient, for the inhibition of tumor cell proliferation.

Embodiments of this aspect of the invention include:

(i) a pharmaceutical composition for the treatment of malignancies in mammals.

(ii) a pharmaceutical composition for the inhibition of growth-factor-dependent tumors.

(iii) a pharmaceutical composition for the inhibition of human breast carcinoma cell proliferation and thereby for the treatment of human breast carcinoma.

(iv) a pharmaceutical composition for the inhibition of the growth stimulatory effect of IGF-I and insulin on tumor cells, as mediated, at least partially, by the IRS-1/GRB2 pathway.

(v) a pharmaceutical composition for the inhibition of mitogenic responses in tumor cells to one or more receptor kinases, growth factors and cytokines of the group consisting of IL-4 and IL-9, for all of which IRS-1 is a substrate, and thereby for the treatment of tumors.

(vi) a pharmaceutical composition for the inhibition of basal, IGF-I-induced and insulin-induced tumor cell proliferation and thereby for the treatment of human breast cancers.

(vii) a pharmaceutical composition wherein said active ingredient is leptin.

The present invention also provides for a method for treating tumors in mammals or for inhibiting tumor cell proliferation in mammals comprising administering to a patient a pharmaceutical composition according to the invention as noted above in a suitable dosage form and by a suitable route of administration. Such dosage forms and routes of administration are usually determined by the professional practitioners following their examination of the patient.

Other aspects and embodiments of the present invention are set forth or will be readily apparent from the following detailed description of the invention.

DETAILED DESCRIPTION OF THE INVENTION

Figure 1:
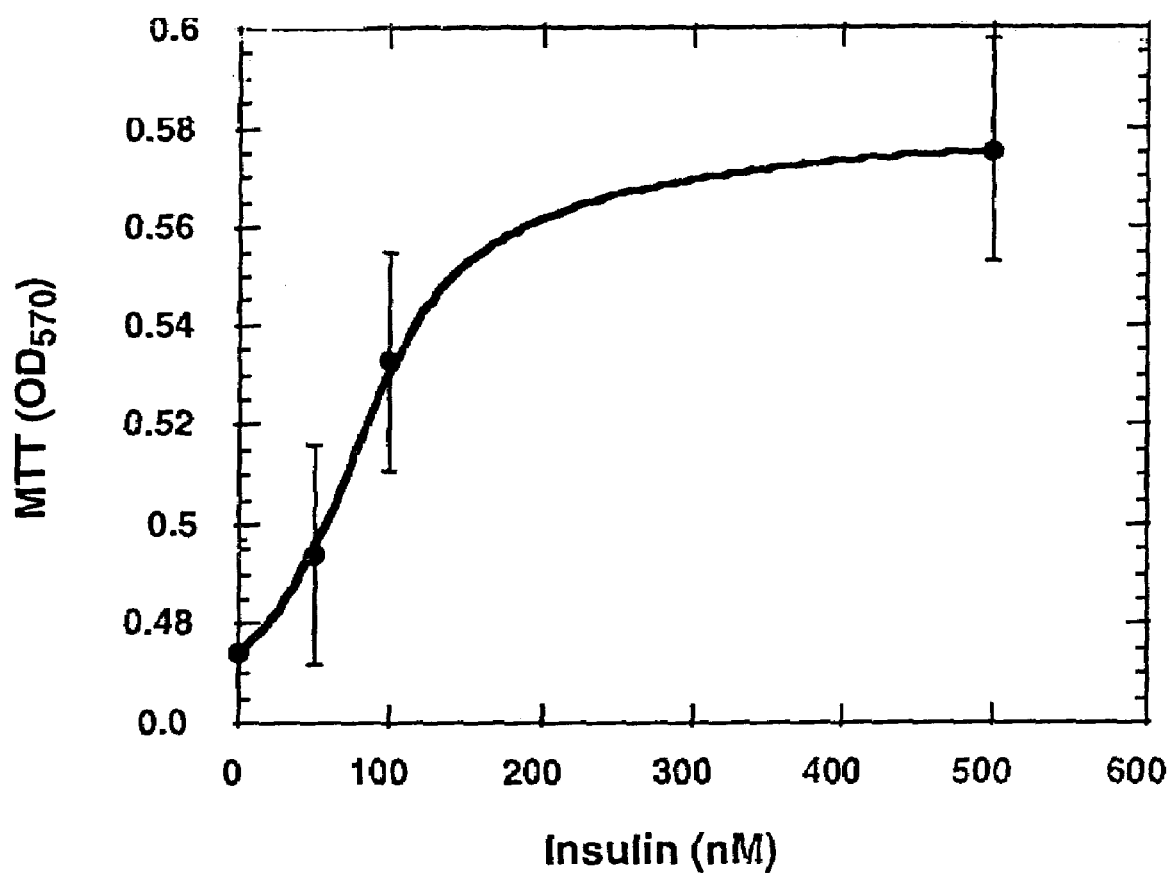
FIG. 1 shows the dependence of T-47D cell proliferation on insulin as determined by MTT staining.

The present invention concerns the use of leptin as an inhibitor of tumor cell proliferation. Typically, cell lines of human origin, derived from various tumors, may be grown in culture in the presence of growth medium supplemented with fetal bovine serum at a concentration of about 10% by volume. Cell proliferation under these conditions is defined hereinafter as "basal cell proliferation". Growth of many tumor cell lines is significantly enhanced when various growth factors such as insulin, epidermal growth factor or insulin-like growth factor-I (IGF-I) are added to the above serum-supplemented culture medium. Inclusion of leptin in growth media at a range of concentrations from 3 to 600 nanomolar reduces both basal cell proliferation and growth-factor-dependent cell proliferation.

The results of the cell culture experiments given in the examples below indicate that leptin is useful for inhibiting the growth of various tumors. Hence, leptin may be useful for the treatment of various malignancies.

In a preferred embodiment of the present invention, leptin is used for the inhibition of breast cancer cell proliferation. When leptin is added to cultures of the human ductal breast carcinoma T-47D cells, (American Type Culture Collection, Rockville, Md.; strain No. ATCC HTB 133), their extent of proliferation is reduced. Similarly, when leptin is added to cultures of the human breast adenocarcinoma MCF7 cells, (American Type Culture Collection, Rockville, Md.; strain No. ATCC HTB 22), their extent of proliferation is reduced. Leptin inhibits both the basal, the IGF-I-induced and the insulin-induced proliferation of T-47D and MCF7 cells. Hence, leptin may be useful specifically for the treatment of breast carcinomas.

The growth stimulatory effect of insulin and IFG-I on cells is mediated, at least in part, via tyrosine phosphorylation of IRS-1 and subsequent association of IRS-1 with GRB2, leading to a mitogenic response. The anti-mitogenic effect of leptin may result from its ability to reduce the basal, the insulin-induced and the IGF-I-induced tyrosine phosphorylation of IRS-1, leading to reduced binding of GRB2 to IRS-1. Furthermore, IRS-1 is a substrate of receptor kinases of other growth factors and cytokines, including IL-4 and IL-9 (Pernis et al., 1995; Yin et al., 1995; Yin et al., 1994). Therefore, leptin may inhibit the mitogenic responses of some or all of the aforementioned growth factors and cytokines, as well as other mitogens, thereby inhibiting the proliferation of a variety of tumor cells.

The present invention further relates to leptin derivatives and analogs, including leptin fusion proteins, leptin muteins, leptin receptor agonists, or active fragments or fractions thereof, and salts of all of same, and pharmaceutical compositions containing leptin, leptin fusion proteins, leptin muteins, leptin receptor agonists, active fractions thereof, or salts of all of same for the treatment of various cancers.

As used herein the term "muteins" refers to analogs of leptin, in which one or more of the amino acid residues are replaced by different amino acid residues, or are deleted, or one or more amino acid residues are added to the original sequence of leptin without changing considerably the activity of the resulting products as compared with wild type leptin or its active fragments or fractions. These muteins are prepared by known synthesis and/or by site-directed mutagenesis techniques, or any other known technique suitable therefor.

Any such mutein preferably has a sequence of amino acids sufficiently duplicative of that of leptin such as to have substantially similar activity to leptin or its active fragments or fractions. Thus, it can be determined whether any given mutein has substantially the same activity as leptin by means of routine experimentation comprising subjecting such a mutein, e.g., to a simple cell proliferation assay, as a mutein which blocks cell proliferation retains sufficient activity of leptin and therefore has at least one of the disclosed utilities of leptin and thus has substantially similar activity thereto.

In a preferred embodiment, any such mutein has at least 40% identity or homology with the sequence of one of the leptins. More preferably, it has at least 50%, at least 60%, at least 70%, at least 80% or, most preferably, at least 90% identity or homology thereto.

Muteins of leptin or its active fragments or fractions which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., *Principles of Protein Structure*, Springer-Verlag, New York, 1978; and Creighton, T. E., *Proteins: Structure and Molecular Properties*, W. H. Freeman & Co., San Francisco, 1983, which are hereby incorporated by reference. For a presentation of nucleotide sequence substitutions, such as codon preferences, see Ausubel et al, supra, at §§ A.1.1–A.1.24, and Sambrook et al, *Current Protocols in Molecular Biology*, Interscience N.Y. §§6.3 and 6.4 (1987, 1992), at Appendices C and D.

Preferred changes for muteins in accordance with the present invention are what are known as "conservative" substitutions. Conservative amino acid substitutions of leptin polypeptides or proteins or its active fragments or fractions may include synonymous amino acids within a group which have sufficiently similar physicochemical properties that substitution between members of the group will preserve the biological function of the molecule, Grantham, *Science*, Vol. 185, pp. 862–864 (1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues, Anfinsen, "Principles That Govern The Folding of Protein Chains", *Science*, Vol. 181, pp. 223–230 (1973). Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are these defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of leptin or its active fractions for use in the present invention include any known method steps, such as presented in U.S. Pat. Nos. RE 33,653, 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

In another preferred embodiment of the present invention, any mutein of leptin or its active fractions for use in the present invention has an amino acid sequence essentially corresponding to that of leptin. The term "essentially corresponding to" is intended to comprehend proteins with minor changes to the sequence of the natural protein which do not affect the basic characteristics of the natural proteins, particularly insofar as its ability to inhibit cell proliferation is concerned. The type of changes which are generally considered to fall within the "essentially corresponding to" language are those which would result from conventional mutagenesis techniques of the DNA encoding leptin, resulting in a few minor modifications, and screening for the desired activity in the manner discussed above.

Muteins in accordance with the present invention include proteins encoded by a nucleic acid, such as DNA or RNA, which hybridizes to DNA or RNA which encodes leptin in accordance with the present invention, under stringent conditions. Such nucleic acid would be a prime candidate to determine whether it encodes a polypeptide which retains the functional activity of leptin of the present invention. The term "stringent conditions" refers to hybridization and subsequent washing conditions which those of ordinary skill in the art conventionally refer to as "stringent". See Ausubel et al., *Current Protocols in Molecular Biology*, supra, Interscience, NY, §§6.3 and 6.4 (1987, 1992), and Sambrook et al., supra. Without limitation, examples of stringent conditions include washing conditions 12–20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30–60 minutes and then a 0.1×SSC and 0.5% SDS at 68° C. for 30–60 minutes. Those of ordinary skill in this art understand that stringency conditions also depend on the length of the DNA sequences, oligonucleotide probes (such as 10–40 bases) or mixed oligonucleotide probes. If mixed probes are used, it is preferable to use tetramethyl ammonium chloride (TMAC) instead of SSC. See Ausubel, supra.

The term "leptin fusion proteins" or simply "fused protein" refers to a polypeptide comprising leptin or its active fractions or a mutein thereof, fused with another protein which, e.g., has an extended residence time in body fluids. Leptin or its active fractions may thus be fused to another protein, polypeptide or the like.

The term "salts" herein refers to both salts of carboxyl groups and to acid addition salts of amino groups of leptin, its active fractions, muteins, or leptin fusion proteins thereof. Salts of a carboxyl group may be formed by means known in the art and include inorganic salts, for example, sodium, calcium, ammonium, ferric or zinc salts, and the like, and salts with organic bases as those formed, for example, with famines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Of course, any such salts must have substantially similar activity to leptin or its active fractions.

"Functional derivatives" as used herein cover derivatives of leptin or its active fragments or fractions and its muteins and leptin fusion proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of leptin, and do not confer toxic properties on compositions containing it. These derivatives may, for example, include polyethylene glycol side-chains which may mask antigenic sites and extend the residence of leptin or its active fractions in body fluids. Other derivatives include aliphatic esters of the carboxyl groups, amides of the carboxyl groups by reaction with ammonia or with primary or secondary famines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fragments or fractions" of leptin, leptin muteins and leptin fusion proteins, the present invention covers any fragment or precursors of the polypeptide chain of leptin, or fused proteins containing any such fragment of leptin, alone or together with associated molecules or residues linked thereto, e.g., sugar or phosphate residues, or aggregates of any of the above derivatives, provided said fraction has substantially similar activity to leptin.

The present invention further relates to use of natural and synthetic agonists of the leptin receptor, which are essentially similar to leptin in their ability to inhibit cell proliferation. Such agonists may be selected from a library of peptides, a library of peptide analogs or a random library of organic molecules. Selection is done by means known in the art, essentially by the ability of the selected agonists to bind to the leptin receptor. For example, a library of random peptides may be prepared as prokaryotic expression plasmids carrying a DNA coding for a random peptide, fused to a carrier protein. Another example is a phage display system in which the expression system is a phage containing DNA coding for a random peptide and incorporated into one of the external phage proteins. Phages coding for fused peptide agonists or antagonists are isolated from the phage library by e.g., panning over surfaces coated with the leptin receptor. Bound phages are isolated and then amplified in bacteria. Several rounds of panning—amplification are usually required in order to obtain phages expressing fused peptides that have high affinity for the leptin receptor. The isolated phage is then amplified and the sequence of DNA coding for the peptide is determined. Alternatively, random peptide libraries or libraries of other molecules are prepared by solid phase synthesis on polymeric beads by means known in the art. Beads carrying a peptide or other molecule having affinity for the leptin receptor are selected from the library, e.g., by binding of labeled leptin receptor, e.g., fluorescently labeled leptin receptor. Positive beads are then picked up and the structure of the peptide or other molecule present on the bead is determined. If the bead carries a peptide, the peptide sequence is determined by protein sequence analysis. If the bead is a representative of a random library of organic molecules then the molecule is cleaved from the bead and its structure is determined by means known in the art, such as mass spectrometry, nuclear magnetic resonance and the like. Candidate peptides identified by their affinity for the leptin receptor are then further selected by their ability to inhibit cell proliferation in the aforementioned manner.

Accordingly, leptin, its active fractions, leptin muteins, leptin fusion proteins, leptin receptor agonists and their salts, functional derivatives, and active fragments or fractions thereof are indicated for the treatment of various malignancies, preferably for growth factor-dependent tumors and more preferably for breast carcinomas.

The present invention further relates to use of pharmaceutical compositions comprising a pharmaceutically acceptable carrier and leptin of the invention, or its active muteins, fused proteins, leptin receptor agonists and their salts, functional derivatives or active fractions thereof.

The pharmaceutical compositions of the invention are prepared for administration by mixing leptin or its derivatives, or leptin receptor agonists with physiologically acceptable carriers, and/or stabilizers and/or excipients, and prepared in dosage form, e.g., by lyophilization in dosage vials. The method of administration can be via any of the accepted modes of administration for similar agents and will depend on the condition to be treated, e.g., intravenously, intramuscularly, subcutaneously, by local injection or topical application, or continuously by infusion, etc. The amount of active compound to be administered will depend on the route of administration, the disease to be treated and the condition of the patient. Local injection, for instance, will require a lower amount of the protein on a body weight basis than will intravenous infusion. Typical active amounts of leptin to be injected are 0.1–1000 microgram/kg body weight and preferably 1 to 10 micrograms/kg. Active amounts of leptin derivatives and leptin receptor agonists may be essentially the same as those of leptin on a molar basis.

Leptin may be administered to cancer patients, e.g., by injection, either alone or in combination with other therapeutic agents or in combination with other therapeutic approaches.

The invention will now be illustrated by the following non-limiting examples:

EXAMPLE 1

Determination of Cell Proliferation by MTT Staining

Reagents:
MTT stock: (3-[4,5-dimethylthiazol-2-yl]-2,5-diphenyltetrazolium bromide 5 mg/ml in phosphate-buffered saline. Stored at $-20°$ C. until used.
Solvent: Conc. HCl (450 microliters) in 2-propanol (100 ml).

Procedure:
Grow cells in 96 well plates in the presence of various growth stimulants and growth inhibitors. At a desired time add MTT stock (10 microliters) to each well. Incubate 2.5–3 hours at 37° C. Aspirate supernatant with vacuum using a fine gauge needle. Add Solvent (100 microliters) and read the absorbance with a microplate reader using a 570 nM filter with background subtraction at 630 nm.

EXAMPLE 2

Determination of Cell Proliferation by Crystal Violet Staining

Procedure:

Grow cells in 96 well plates in the presence of various growth stimulants and growth inhibitors. At the desired time add 12.5% glutaraldehyde (40 microliters) to each well. Incubate 30 minutes at room temperature. The microplate was then washed with water, dried and aq. crystal violet (0.1%, 0.1 ml) was added to each well. The microplate was further incubated for 30 min., washed with water and read at 540 nm with background subtraction at 630 nm.

EXAMPLE 3

Determination of the Insulin-dependent T-47D Cell Proliferation

Human T-47D cells (American Type Culture Collection, Rockville, Md., strain No. ATCC HTB 133), were seeded into 96 well plates at $3 \times 10^5$ cells/ml in DMEM and 10% fetal bovine serum (FBS), 0.1 ml per well. Human insulin was added to different wells at increasing concentrations, the plates were incubated for 72 hours and the number of cells was then determined by staining with MTT (FIG. 1). The results are average of 8 replicates. Based on the extent of cell proliferation as shown in FIG. 1, a concentration of 50 nM insulin was used for further studies.

EXAMPLE 4

Determination of the IGF-I-dependent T-47D Cell Proliferation

Figure 2:
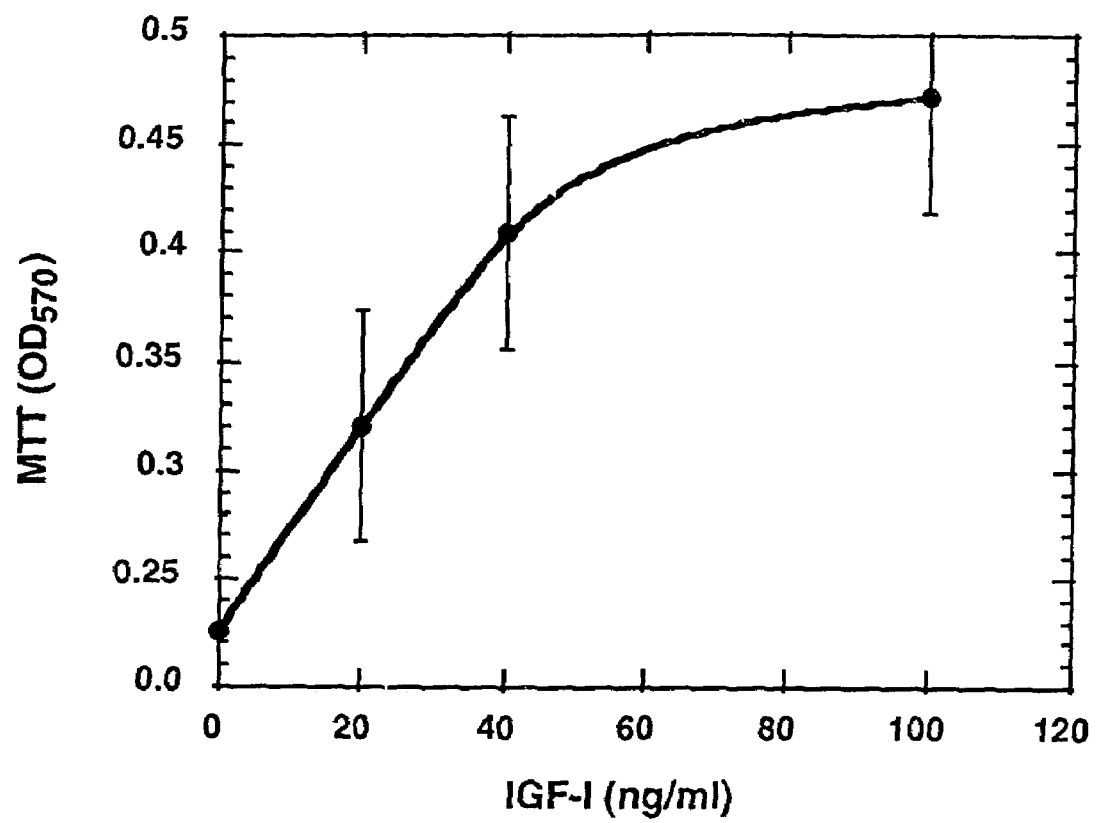
FIG. 2 shows the dependence of T-47D cell proliferation on IGF-I as determined by MTT staining.

Human T-47D cells were seeded into 96 well plates at $3 \times 10^5$ cells/ml in DMEM and 10% FBS, 0.1 ml per well. Human IGF-I was added to different wells at increasing concentrations, the plates were incubated for 3 days and the number of cells was then determined by MTT staining (FIG. 2). The results are average of 8 replicates. Based on the extent of cell proliferation as shown in FIG. 2, a concentration of 50 ng/ml IGF-I was used for further studies.

EXAMPLE 5

Inhibition of Insulin-induced T-47D Cell Proliferation by Leptin

Figure 3:
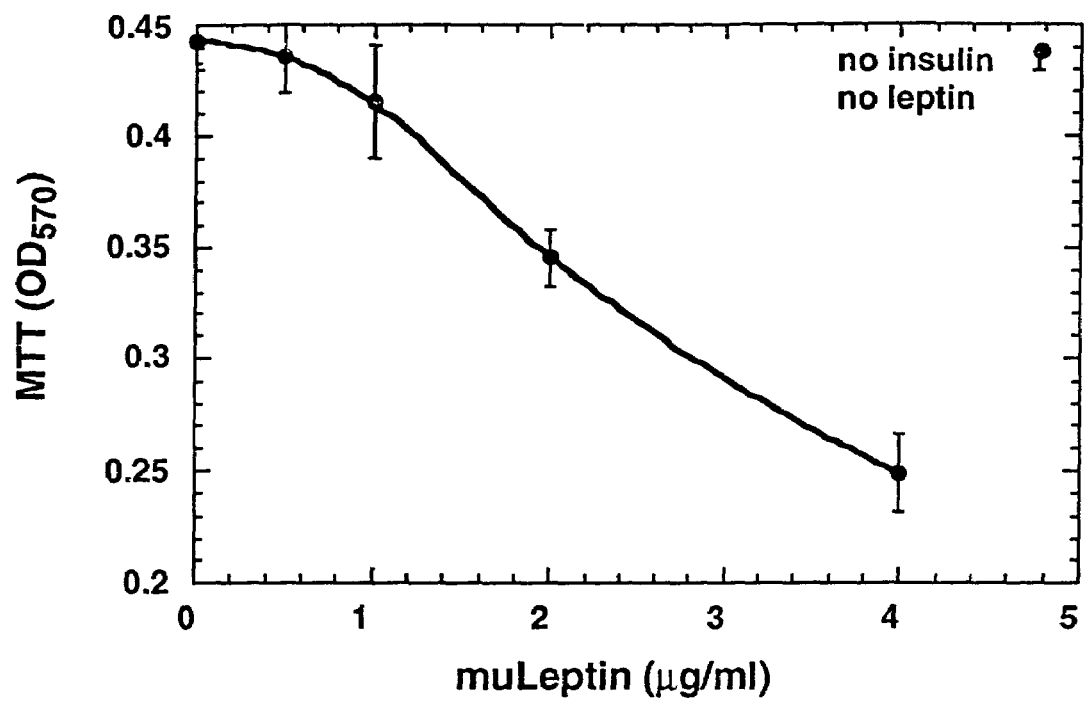
FIG. 3 shows the inhibition of insulin-induced T-47D cell proliferation in 10% fetal bovine serum (FBS) by murine leptin as determined by MTT staining.

T-47D cells ($3 \times 10^5$ cells/ml) in DMEM supplemented with 10% FBS were seeded into 96 well plates (0 1 ml per well). Cells were treated with insulin (50 nM), with or without the indicated concentrations of murine leptin. The Plates were incubated at 37° C. in 5% $CO_2$ for 48 hours. The cells were then stained with MTT. The data are mean ± standard error (SE, n=8). The results show that leptin inhibited significantly the insulin-induced cell proliferation (FIG. 3).

Figure 4:
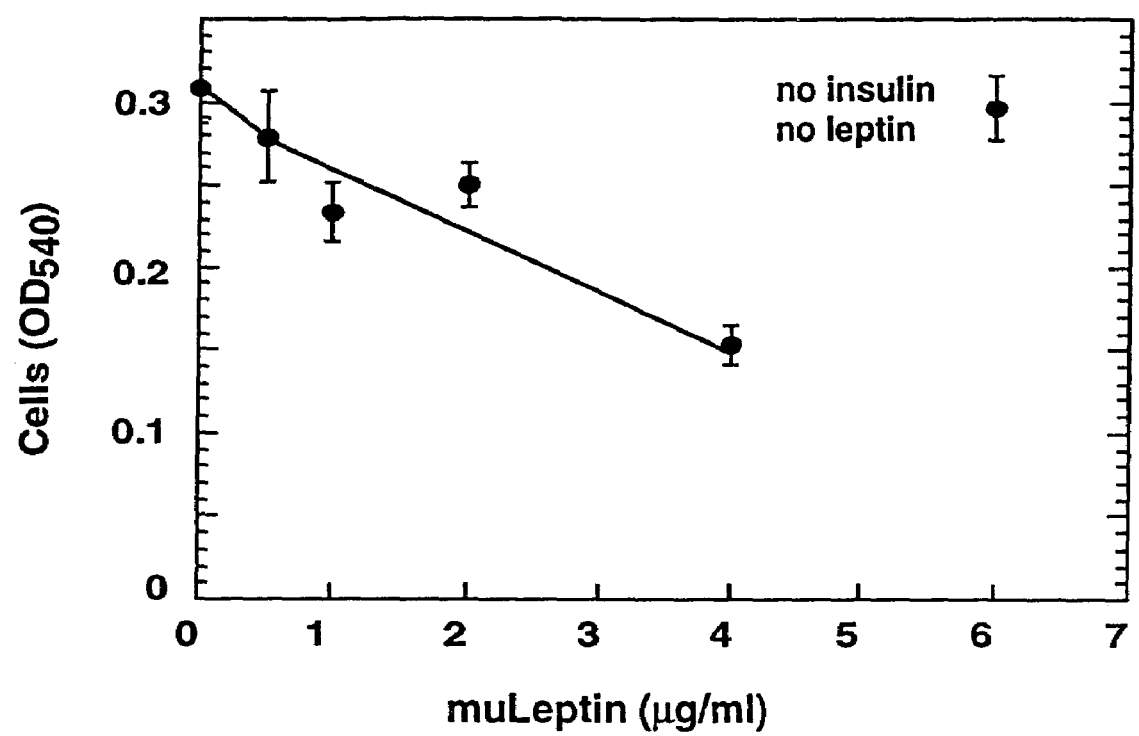
FIG. 4 shows the inhibition of insulin-induced T-47D cell proliferation in 2% FBS by murine leptin as determined by crystal violet staining.

T-47D cells ($3 \times 10^5$ cells/ml) in DMEM supplemented with 10% FBS were seeded into 96 well plates (0.1 ml per well). After one day the medium was replaced by DMEM supplemented with 2% FBS and after one day the cells were treated with insulin (50 nM), with or without the indicated concentrations of murine leptin in DMEM-2% FBS. The Plates were incubated at 37° C. in 5% $CO_2$ for 48 hours. The cells were then stained with crystal violet. The data are mean ± SE, (n=8). The results show that leptin inhibited significantly the insulin-induced cell proliferation (FIG. 4).

EXAMPLE 6

Inhibition of IGF-I-induced T-47D Cell Proliferation by Leptin

Figure 5:
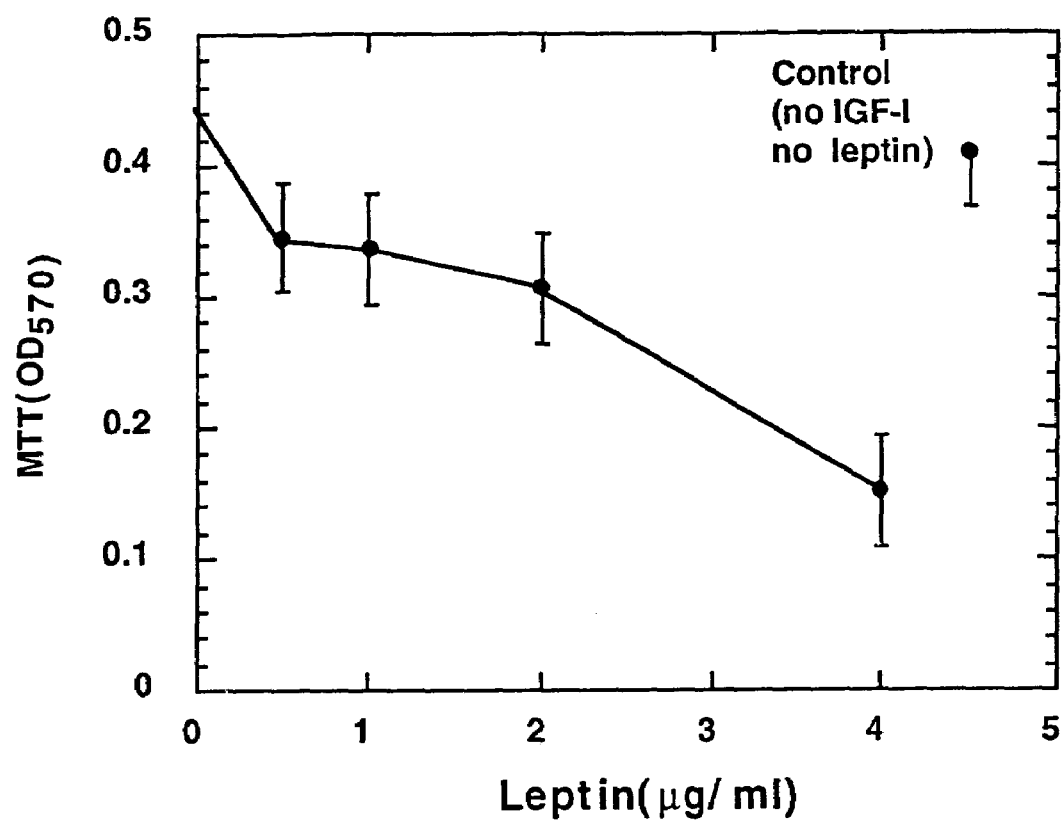
FIG. 5 shows the inhibition of IGF-I-induced T-47D cell proliferation in 10% FBS by murine leptin as determined by MTT staining.

T-47D cells ($3 \times 10^5$ cells/ml) in DMEM supplemented with 10% FBS were seeded into 96 well plates (0.1 ml per well). Cells were treated with IGF-I (50 ng/ml), with or without the indicated concentrations of murine leptin. The Plates were incubated at 37° C. in 5% $CO_2$ for 48 hours. The cells were then stained with MTT. The data are mean ± standard error (SE, n=8). The results show that leptin inhibited significantly the IGF-I-induced cell proliferation (FIG. 5).

Figure 6:
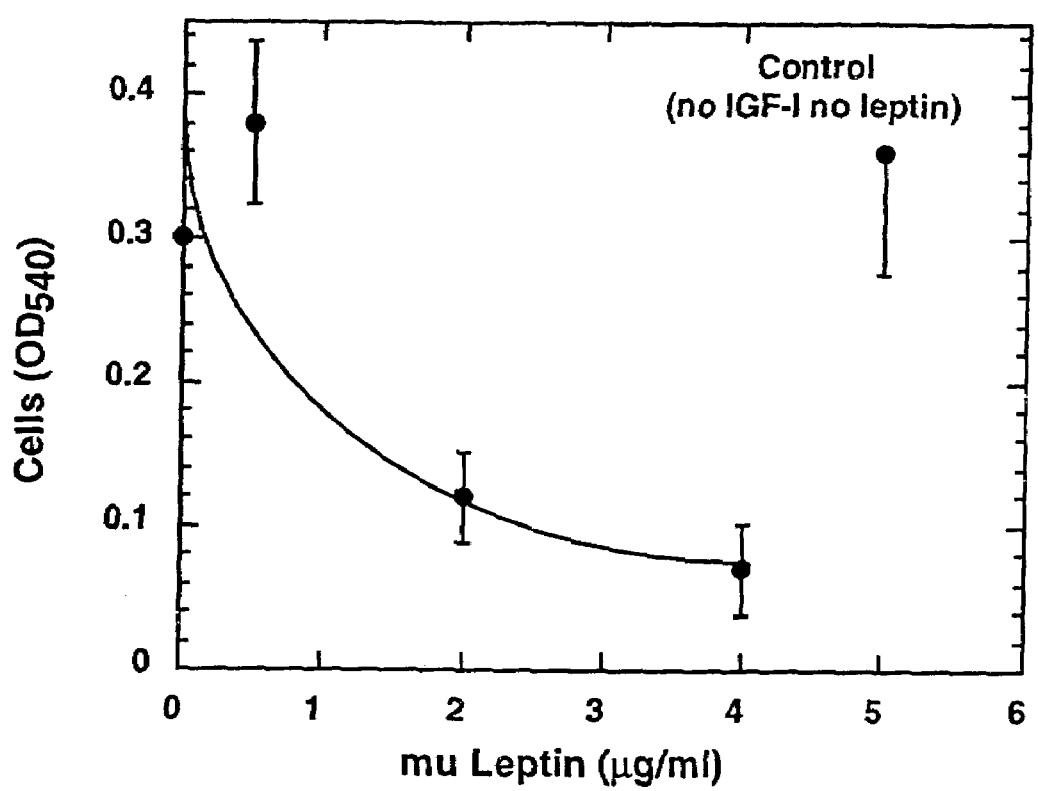
FIG. 6 shows the inhibition of IGF-I-induced T-47D cell proliferation in 2% FBS by murine leptin as determined by crystal violet staining.

T-47D cells ($3 \times 10^5$ cells/ml) in DMEM supplemented with 10% FBS were seeded into 96 well plates (0.1 ml per well). After one day the medium was replaced by DMEM supplemented with 2% FBS and after one day the cells were treated with IGF-I (50 ng/ml), with or without the indicated concentrations of murine leptin in DMEM-2% FBS. The Plates were incubated at 37° C. in 5% $CO_2$ for 48 hours. The cells were then stained with crystal violet. The data are mean ± standard error (SE, n=8). The results show that leptin inhibited significantly the IGF-I-induced cell proliferation (FIG. 6).

Figure 7:
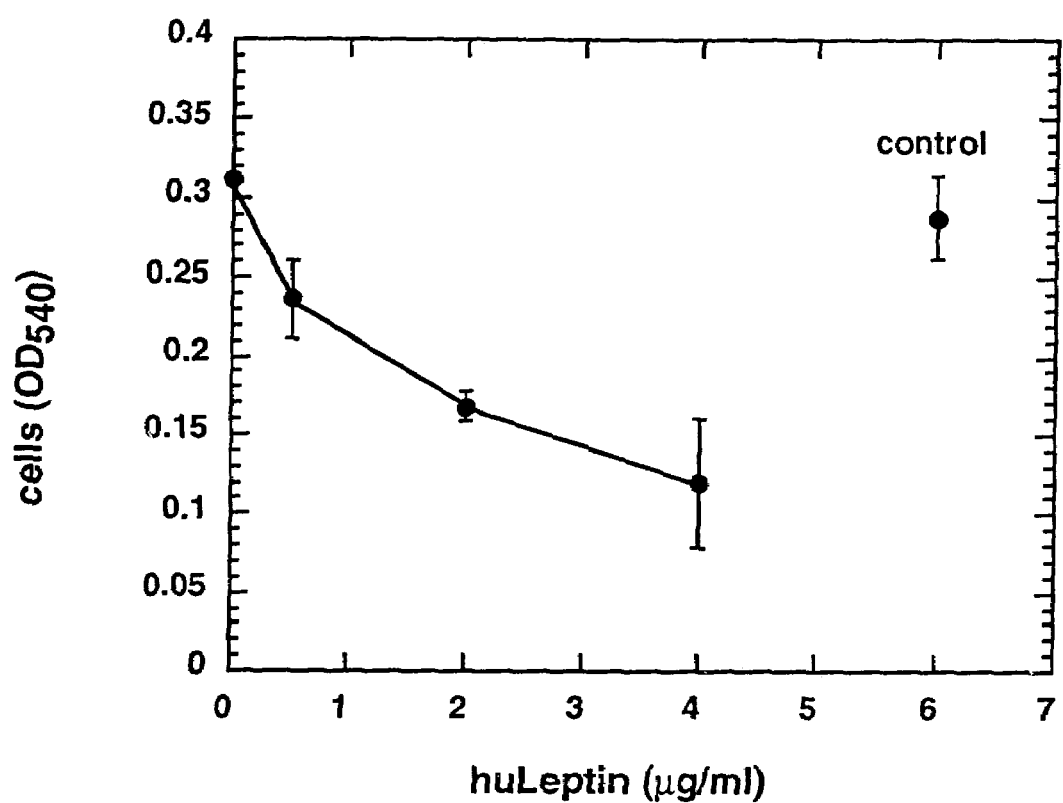
FIG. 7 shows the inhibition of IGF-I-induced T-47D cell proliferation in 2% FBS by human leptin as determined by crystal violet staining.

T-47D cells ($3 \times 10^5$ cells/ml) in DMEM supplemented with 10% FBS were seeded into 96 well plates (0.1 ml per well). After one day the medium was replaced by DMEM supplemented with 2% FBS and after one day the cells were treated with IGF-I (50 ng/ml), with or without the indicated concentrations of human leptin in DMEM-2% FBS. The Plates were incubated at 37° C. in 5% $CO_2$ for 48 hours. The cells were then stained with crystal violet. The data are mean ± standard error (SE, n=8). The results show that leptin inhibited significantly the IGF-I-induced cell proliferation (FIG. 7).

EXAMPLE 8

Inhibition of Insulin-induced MCF7 Cell Proliferation by Leptin

Figure 8:
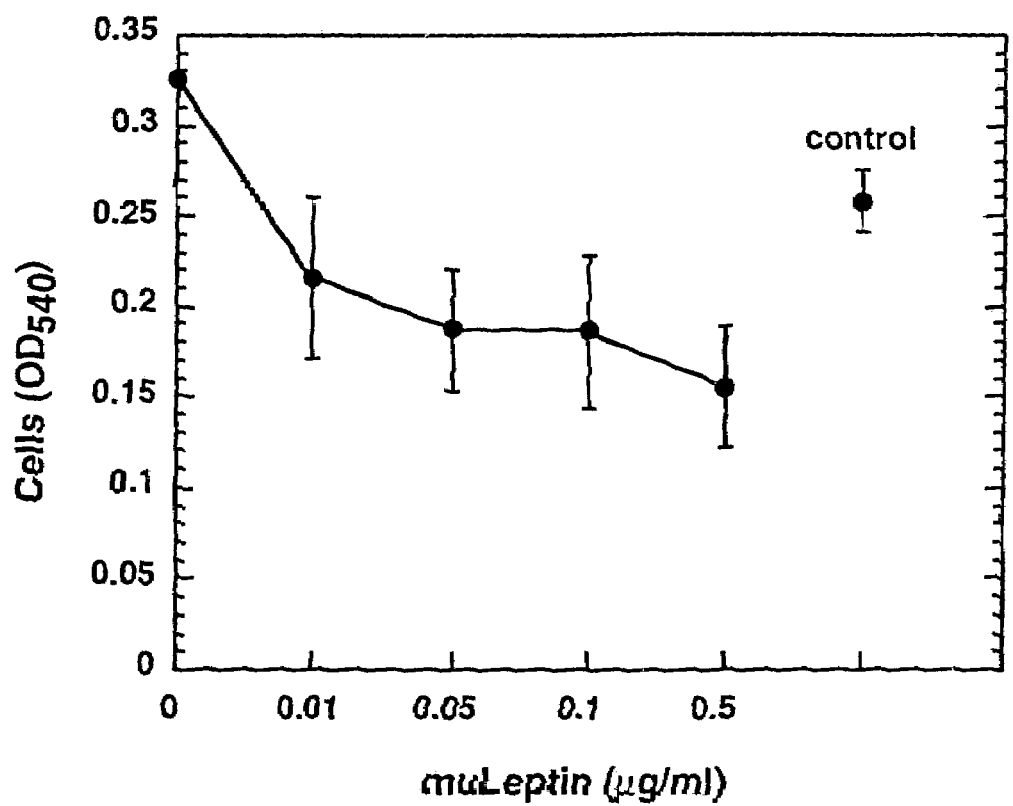
FIG. 8 shows the inhibition of insulin-induced MCF7 cell proliferation in serum-free by murine leptin as determined by crystal violet staining.

Human breast adenocarcinoma MCF7 cells ($3 \times 10^4$ cells/ml, American Type Culture Collection, Rockville, Md.; strain No. ATCC HTB 22) supplemented with 6% FBS were seeded into 96 well plates (0.1 ml per well). After one day the medium was replaced by serum-free DMEM and after one day the cells were treated with insulin (50 nM) with or without the indicated concentrations of murine leptin in a serum-free medium. The Plates were incubated at 37° C. in 5% $CO_2$ for 48 hours. The cells were then stained with crystal violet. The data are mean ± SE, (n=8). The results show that leptin inhibited significantly the insulin-induced cell proliferation (FIG. 8).

EXAMPLE 9

Inhibition of IGF-I-induced MCF7 Cell Proliferation by Leptin

Figure 9:
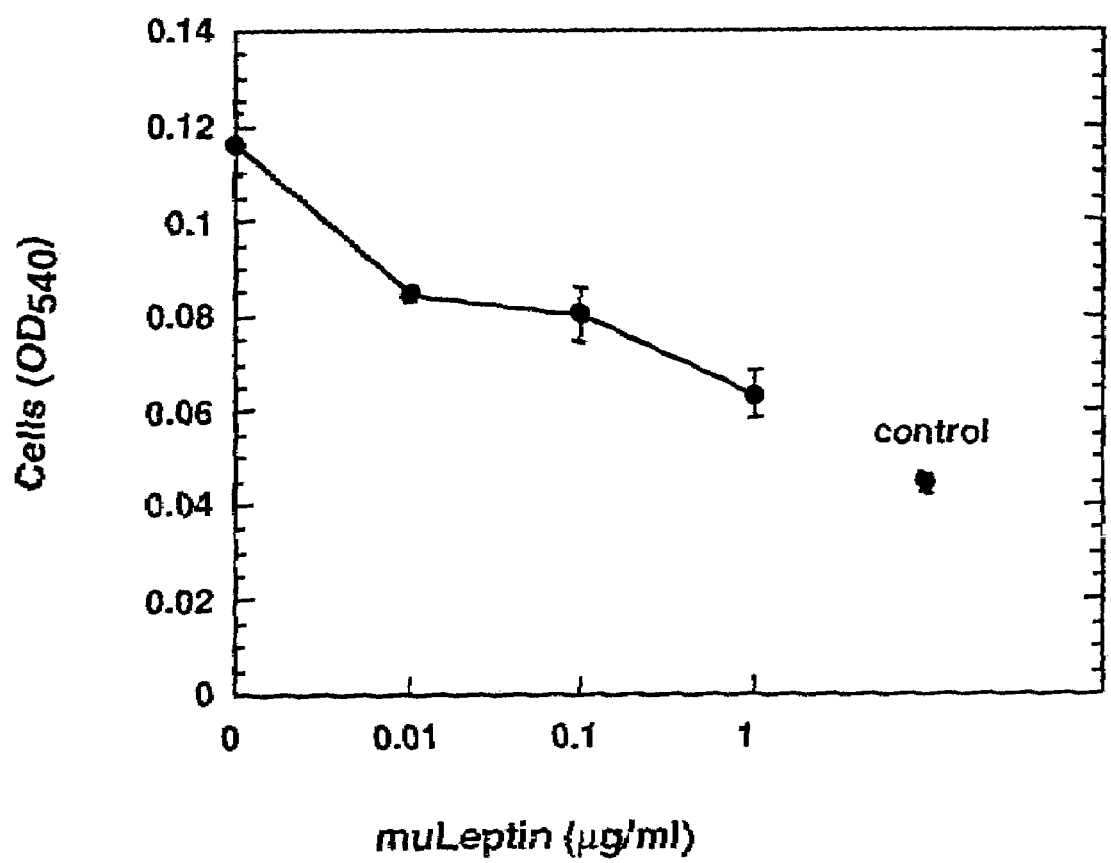
FIG. 9 shows the inhibition of IGF-I-induced MCF7 cell proliferation in serum-free by murine leptin as determined by crystal violet staining.

Human breast adenocarcinoma MCF7 cells in DMEM supplemented with 10% FBS were seeded into 96 well plates ($3 \times 10^4$ cells/ml, 0.1 ml per well). After one day the medium was replaced by a serum-free medium. After one day the cells were treated with IGF-I (50 ng/ml) with or without the indicated concentrations of murine leptin in a serum-free medium. The Plates were incubated at 37° C. in 5% $CO_2$ for 96 hours. The cells were then stained with crystal violet. The data are mean ± SE, (n=8). The results show that leptin inhibited significantly the insulin-induced cell proliferation (FIG. 9).

REFERENCES

Araki, E., Lipes, M. A., Patti, M. E., Bruning, J. C. Haag. B. r., Johnson, R. S., and Kahn, C. R. (1994). Alternative pathway of insulin signalling in mice with targeted disruption of the IRS-1 gene [see comments]. Nature 372, p186–90.

Ausubel, F. M. et al., eds., Current Protocols In Molecular Biology.

Campfield, L. A., Smith, F. J., Guisez, Y., Devos, R., and Burn, P. (1995). Recombinant mouse OB protein: Evidence for a peripheral signal linking adiposity and central neural networks. Science 269, 546–549.

Cheatham, B., and Kahn, C. R. (1995). Insulin action and the insulin signaling network. Endocr Rev 16, p117–42.

Cioffi, J. A., Shafer, A. W., Zupancic, T. J., Smith-Gbur, J., Mikhail, A., Platika, D., and Snodgrass, H. R. (1996). Novel B219/OB receptor isoforms: Possible role of leptin in hematopoiesis and reproduction. Nature Medicine 2, 585–589.

Cohen, B., Novick, D., and Rubinstein, M. (1996). Modulation of insulin activities by leptin. Science 274, 1185–1188.

Collins, S., Kuhn, C. M., Petro, A. E., Swick, A. G., Chrunyk, B. A., and Surwit, R. S. (1996). role of leptin in fat regulation. Nature 380, 677.

Considine, R. V., Sinha, M. K., Heiman, M. L., Kriauciunas, A., Stephens, T. W., Nyce, M. R., Ohannesian, J. P., Marco, C. C., Mckee, L. J., Bauer, T. L., and Caro, J. F. (1996). Serum immunoreactive leptin concentrations in normal-weight and obese humans. N Engl J Med 334, 292–295.

Felber, J. P., and Golay, A. (1995). Regulation of nutrient metabolism and energy expenditure. Metabolism 44, Suppl 2) p4–9.

Frederich, R. C., Hamann, A., Anderson, S., Lollmann, B., Lowell, B. B., and Flier, J. S. (1995). Leptin levels reflect body lipid content in mice: Evidence for diet-induced resistance to leptin action. Nature Med 1, 1311–1314.

Halaas, J. L., Gajiwala, K. S., Maffei, M., Cohen, S. L., Chait, B. T., Rabinowitz, D., Lallone, R. L., Burley, S. K., and Friedman, J. M. (1995). Weight-reducing effects of the plasma protein encoded by the obese gene [see comments]. Science 269, p543–6.

Lee, G. H., Proenca, R., Montez, J. M., Carroll, K. M., Darvishzadeh, J. G., Lee, J. I., and Friedman, J. M. (1996). Abnormal splicing of the leptin receptor in diabetic mice. Nature 379, 632–635.

Lonnqvist, F., Arner, P., Nordfors, L., and Schalling, M. (1995). Overexpression of the obese (ob) gene in adipose tissue of human obese subjects. Nature Med 1, 950–953.

Maffei, M., Halaas, J., Ravussin, E., Pratley, R. E., Lee, G. H., Zhang, Y., Fei, H., Kim, S., Lallone, R., Ranganathan, S., Kern, P. A., and Friedman, J. M. (1995). Leptin levels in human and rodent: Measurement of plasma leptin and ob RNA in obese and weight-reduced subjects. Nature Med 1, 1155–1161.

Milazzo, G., Sciatta, L., Papa, V., Goldfine, I. D., and Vigneri, R. (1997). ASPB-10 insulin induction of increased mitogenic responses and phenotypic changes in human breast epithelial cells: evidence for enhanced interactions with the insulin-like growth factor-1 receptor. Molec. Carcinogenesis 18, 19–25.

Millazzo, G., Giorgino, F., Damante, G., Sung, C., Stampfer, M. R., Vigneri, R., Goldfine, I., and Belfiore, A. (1992). Insulin receptor expression in human breast cancer cell lines. Cancer Res. 52, 3924–3930.

Myers, M. G., Jr., Sun, X. J., Cheatham, B., Jachna, B. R., Glasheen, E. M., Backer, J. M., and White, M. F. (1993). IRS-1 is a common element in insulin and insulin-like growth factor-I signaling to the phosphatidylinositol 3'-kinase. Endocrinology 132, p1421–30.

Myers, M. G., Jr., Sun, X. J., and White, M. F. (1994). The IRS-1 signaling system. Trends Biochem Sci 19, p289–93.

Myers, M. G., Jr., Wang, L. M., Sun, X. J., Zhang, Y., Yenush, L., Schlessinger, J., Pierce, J. H., and White, M. F. (1994). Role of IRS-1-GRB-2 complexes in insulin signaling. Mol Cell Biol 14, p3577–87.

Myers, M. G., Jr., and White, M. F. (1993). The new elements of insulin signaling. Insulin receptor substrate-1 and proteins with SH2 domains. Diabetes 42, p643–50.

Pelleymounter, M. A., Cullen, M. J., Baker, M. B., Hecht, R., Winters, D., Boone, T., and Collins, F. (1995). Effects of the obese gene product on body weight regulation in ob/ob mice [see comments]. Science 269, p540–3.

Pernis, A., Witthuhn, B., Keegan, A. D., Nelms, K., Garfein, E., Ihle, J. N., Paul, W. E., Pierce, J. H., and Rothman, P. (1995). Interleukin 4 signals through two related pathways. Proc Natl Acad Sci USA 92, 7971–7975.

Rose, D. W., Saltiel, A. R., Majumdar, M., Decker, S. J., and Olefsky, J. M. (1994). Insulin receptor substrate 1 is required for insulin-mediated mitogenic signal transduction. Proc Natl Acad Sci USA 91, p797–801.

Sambrook et al., (1989) Molecular cloning: A laboratory Manual, Cold Spring Harbor Laboratory Press, Cold Spring Harbor, N.Y.

Tamemoto, H., Kadowaki, T., Tobe, K., Yagi, T., Sakura, H., Hayakawa, T., Terauchi, Y., Ueki, K., Kaburagi, Y., Satoh, S., and et al. (1994). Insulin resistance and growth retardation in mice lacking insulin receptor substrate-1 [see comments]. Nature 372, p182–6.

Tartaglia, L. A., Dembski, M., Weng, X., Deng, N. H., Culpepper, J., Devos, R., Richards, G. J., Campfield, L. A., Clark, F. T., Deeds, J., Muir, C., Sanker, S., Moriarty, A., Moore, K. J., Smutko, J. S., Mays, G. G., Woolf, E. A., Monroe, C. A., and Tepper, R. I. (1995). Identification and expression cloning of a leptin receptor, OB-R. Cell 83, 1263–1271.

Weigle, D. S., Bukowski, T. R., Foster, D. C., Holderman, S., Kramer, J. M., Lasser, G., Loftonday, C. E., Prunkard, D. E., Raymond, C., and Kuijper, J. L. (1995). Recombinant ob protein reduces feeding and body weight in the ob/ob mouse. J Clin Invest 96, 2065–2070.

White, M. F., and Kahn, C. R. (1994). The insulin signaling system. J Biol Chem 269, p1–4.

Yin, T. G., Keller, S. R., Quelle, F. W., Witthuhn, B. A., Tsang, M. L. S., Lienhard, G. E., Ihle, J. N., and Yang, Y. C.

(1995). Interleukin-9 induces tyrosine phosphorylation of insulin receptor substrate-1 via JAK tyrosine kinases. J Biol Chem 270, 20497–20502.

Yin, T. G., Tsang, M. L. S., and Yang, Y. C. (1994). JAK1 kinase forms complexes with interleukin-4 receptor and 4PS/insulin receptor substrate-1-like protein and is activated by interleukin-4 and interleukin-9 in T lymphocytes. J Biol Chem 269, 26614–26617.

Zhang, Y., Proenca, R., Maffei, M., Barone, M., Leopold, L., and Friedman, J. M. (1994). Positional cloning of the mouse obese gene and its human homologue. Nature 372, 425–432.

The invention claimed is:

1. A method for treating tumors in mammals or for inhibiting tumor cell proliferation in mammals, comprising administering to a mammal in need thereof an effective amount of an active agent selected from the group consisting of
   (a) leptin;
   (b) a mutein of leptin having at least 90% identity with the sequence of a leptin and has the ability to inhibit the IGF-1 induced or insulin-induced proliferation of the human breast cancer cell line T-47D or MCF7, or having a sequence encoded by a nucleic acid that hybridizes to a nucleic acid which encodes leptin under stringent conditions that include washing conditions 12–20° C. below the calculated Tm of the hybrid under study, and has the ability to inhibit the IGF-1 induced or insulin-induced proliferation of the human breast cancer cell line T-47D or MCF7;
   (c) a fragment of one of (a) or (b) which has the ability to inhibit the IGF-I induced or insulin-induced proliferation of the human breast cancer cell line T-47D or MCF7;
   (d) a fusion protein comprising (a), (b) or (c);
   (e) a salt of any one of (a)–(d); and
   (f) a functional derivative of any of (a)–(d) selected from the group consisting of one or more polyethylene glycol side chains formed by means of functional groups which occur as side chains of any of (a)–(d), aliphatic esters of one or more carboxyl groups, amides of one or more carboxyl groups by reaction with ammonia or with primary or secondary famines, N-acyl derivatives of one or more free amino groups of the amino acid residues formed with acyl moieties, O-acyl derivatives of free hydroxyl groups formed with acyl moieties, and combinations thereof.

2. The method according to claim 1 for inhibiting cell proliferation for the treatment of malignancies in mammals, wherein the mammal is one in need of treatment of a malignancy.

3. The method according to claim 1 for inhibiting growth-factor dependent tumors, wherein the mammal is one in need of inhibition of a growth-factor dependent tumor.

4. The method according to claim 1 for inhibiting human breast carcinoma cell proliferation, wherein the mammal is one in need of inhibition of human breast carcinoma cell proliferation.

5. The method according to claim 4 for treatment of human breast carcinomas, wherein the mammal is one in need of treatment of human breast carcinoma.

6. The method according to claim 1 for inhibiting the growth stimulatory effect of insulin on tumor cells, as mediated, at least partially, by the insulin receptor substrate-1 (IRS-1)/growth-factor receptor-associated binding protein-2 (GRB2) pathway, wherein the mammal is one in need of inhibition of the growth stimulatory effect of insulin on tumor cells.

7. The method according to claim 1 for inhibiting the mitogenic responses in tumor cells to one or more receptor kinases, growth factors and cytokines of the group consisting of IGF-1, IL-4 and IL-9, for all of which IRS-1 is a substrate, for the treatment of tumors, wherein the mammal is one in need of treatment of a tumor.

8. The method according to claim 1 for inhibiting basal and insulin-induced tumor cell proliferation for the treatment of human breast cancers, wherein the mammal is one in need of treatment of human breast cancer.

9. A method in accordance with claim 1, wherein said active agent is leptin.

10. A method in accordance with claim 1, wherein said active agent is a mutein of leptin having at least 90% identity with the sequence of a leptin and has the ability to inhibit the IGF-I induced or insulin-induced proliferation of the human breast cancer cell line T-47D or MCF7.

11. A method in accordance with claim 1, wherein said active agent is a mutein of leptin having a sequence encoded by a nucleic acid which hybridizes to a nucleic acid which encodes leptin under stringent conditions that include washing conditions 12–20° C. below the calculated Tm of the hybrid under study, and has the ability to inhibit the IGF-I-induced or insulin-induced proliferation of the human breast cancer cell line T-47D or MCF7.

12. A method in accordance with claim 1, wherein said active agent is a fragment of (a) or (b) of claim 1, which has the ability to inhibit the IGF-I-induced or insulin-induced proliferation of the human breast cancer cell line T-47D or MCF7.

13. A method in accordance with claim 12, wherein said active agent is a fragment of leptin which has the ability to inhibit the IGF-I-induced or insulin-induced proliferation of the human breast cancer cell line T-47D or MCF7.

14. A method in accordance with claim 1, wherein said active agent is a fusion protein comprising (a), (b) or (c) of claim 1.

15. A method in accordance with claim 14, wherein said active agent is a fusion protein comprising leptin.

16. A method in accordance with claim 1, wherein said active agent comprises a mutein of leptin having at least 90% identity with the sequence of a leptin and has the ability to inhibit the IGF-I-induced or insulin-induced proliferation of the human breast cancer cell line T-47D or MCF7.

17. A method for treating human breast carcinoma or for inhibiting human breast carcinoma cell proliferation, comprising administering to a patient in need thereof an effective amount of an active agent selected from the group consisting of:
   (a) leptin;
   (b) a mutein of leptin having at least 90% identity with the sequence of a leptin and has the ability to inhibit the IGF-I induced or insulin-induced proliferation of the human breast cancer cell line T-47D or MCF7, or having a sequence encoded by a nucleic acid that hybridizes to a nucleic acid which encodes leptin under stringent conditions that include washing conditions 12–20° C. below the calculated Tm of the hybrid under study, and has the ability to inhibit the IGF-1 induced or insulin-induced proliferation of the human breast cancer cell line T-47D or MCF7;

(c) a fragment of one of (a) or (b) which has the ability to inhibit the IGF-I induced or insulin-induced proliferation of the human breast cancer cell line T-47D or MCF7;

(d) a fusion protein comprising (a), (b) or (c);

(e) a salt of any one of (a)–(d); and (f) a functional derivative of any of (a)–(d) selected from the group consisting of one or more polyethylene glycol side chains formed by means of functional groups which occur as side chains of any of (a)–(d), aliphatic esters of one or more carboxyl groups, amides of one or more carboxyl groups by reaction with ammonia or with primary or secondary famines, N-acyl derivatives of one or more free amino groups of the amino acid residues formed with acyl moieties, O-acyl derivatives of free hydroxyl groups formed with acyl moieties, and combinations thereof.

18. A method in accordance with claim 17, wherein said active agent is selected from the group consisting of:

(i) leptin;

(ii) a fragment of leptin that has the ability to inhibit the IGF-I induced or insulin-induced proliferation of the human breast cancer cell line T-47D or MCF7;

(iii) a fusion protein comprising (i) or (ii);

(iv) a salt of any of (i)–(iii); and (v) a functional derivative of any of (i)–(iii) selected from the group consisting of one or more polyethylene glycol side chains formed by means of functional groups which occur as side chains of any of (a)–(d), aliphatic esters of one or more carboxyl groups, amides of one or more carboxyl groups by reaction with ammonia or with primary or secondary famines, N-acyl derivatives of one or more free amino groups of the amino acid residues formed with acyl moieties, O-acyl derivatives of free hydroxyl groups formed with acyl moieties, and combinations thereof.

* * * * *